United States Patent [19]
Lazzara et al.

[11] Patent Number: 4,988,298
[45] Date of Patent: Jan. 29, 1991

[54] PRECISION ABUTMENT BASE

[75] Inventors: Richard J. Lazzara, Lake Worth; Keith D. Beaty, West Palm Beach, both of Fla.

[73] Assignee: Implant Innovations, Inc., West Plam Beach, Fla.

[21] Appl. No.: 299,078

[22] Filed: Jan. 23, 1989

[51] Int. Cl.$^5$ ............................................. A61C 8/00
[52] U.S. Cl. ................................. 433/173; 433/174; 433/202.1
[58] Field of Search ............... 433/173, 174, 175, 176, 433/169, 201.1, 202.1, 204, 206, 208

[56] References Cited

U.S. PATENT DOCUMENTS

| | | | |
|---|---|---|---|
| 3,624,904 | 12/1971 | Linkow | 433/173 |
| 3,722,094 | 3/1973 | Rivoir | 433/204 |
| 3,732,621 | 5/1973 | Bostrom | 433/174 |
| 4,229,170 | 10/1980 | Perez | 433/202.1 X |
| 4,318,696 | 3/1982 | Kasawa et al. | 433/173 |
| 4,657,510 | 4/1987 | Gittleman | 433/173 |
| 4,713,004 | 12/1987 | Linkow et al. | 433/174 |
| 4,756,689 | 7/1988 | Lundgren et al. | 433/173 |
| 4,758,160 | 7/1988 | Ismail | 433/173 |

FOREIGN PATENT DOCUMENTS

| | | | |
|---|---|---|---|
| 0126624 | 11/1984 | European Pat. Off. | 433/174 |
| 0288445 | 10/1988 | European Pat. Off. | 433/173 |
| 3406448 | 8/1984 | Fed. Rep. of Germany | 433/174 |
| 88/03391 | 5/1988 | World Int. Prop. O. | 433/174 |

*Primary Examiner*—Robert P. Swiatek
*Assistant Examiner*—Nicholas D. Lucchesi
*Attorney, Agent, or Firm*—Alfred H. Rosen

[57] ABSTRACT

A Precision-machined abutment base for accurately fixing an artificial tooth to a dental implant fixture is fashioned of a dental gold alloy or other machinable rigid dental material in a tubular form having an internal retainer for fixing it to the implant fixture, and external retainers for anchoring it to a rigid substructure of the tooth and to an anatomical overlay covering the substructure. An artificial tooth is disclosed in which the substructure is a casting of the same material as the abutment base, forming a unit with the base, is covered with an overlay of porcelain that is bonded at its gingival end directly to a marginal portion of the abutment base, completely concealing the substructure.

5 Claims, 1 Drawing Sheet

PRECISION ABUTMENT BASE

BACKGROUND OF THE INVENTION

This invention relates in general to restorative dentistry, and more particularly to methods and means for fixing a permanent dental restoration to an underlying support such as a dental implant fixture or the like. The invention provides for the fabrication and use of fixed restorations in partially edentulous patients undergoing treatment with osseointegrated fixtures.

While the field of restorative dentistry has made significant advances in the use of dental implants to support dental restorations intended to replace natural teeth, and intended for long-lasting use, there remains a need to provide simple, reliable, cosmetically-attractive permanent single-tooth restorations supported on a dental implant fixture. A dental bridge supported on two or more abutments is not subjected to forces that would induce it to rotate around an abutment, but a single-tooth restoration can rotate, or pivot, around its underlying support. Consequently, practitioners of restorative dentistry even now find it advisable, even necessary, to attach a single-tooth restoration to an adjacent tooth in order to prevent such rotating or pivoting.

A single-tooth restoration presents unique problems when it is supported on an implanted fixture. Such fixtures in common use are generally around 4 mm. in diameter. Even after succsessful osseointegration a platform that is about 4 mm. in diameter provides a small bearing surface on which to support an artificial tooth. The danger that screws or pins used to attach the restoration to the implant fixture will break or bend in use in ever-present. It is among the purposes of this invention to reduce or eliminate this danger, as well as to provide a single-tooth restoration that can be non-rotatively fixed on a dental implant fixture without requiring support from an adjacent tooth or abutment, will be simple to fabricate, reliable in use, and cosmetically pleasing.

GENERAL NATURE OF THE INVENTION

A widely-used form of dental implant fixture consists essentially of a generally cylindrical body adapted to be implanted in a cylindrical bore made in the alveolar ridge crest of a patient's edentulous jawbone after the gum tissue has been displaced, and having an internally-threaded cylindrical socket in which to fasten a component used for attaching a permanent dental restoration to the implant fixture. A coronal end of the fixture has at its gingival aspect a transverse surface that is flush or nearly flush with the alveolar ridge crest of the jawbone after the fixture has been implanted in it. The invention is illustrated and described hereinafter with reference to implant fixtures taking that form, but this exemplary only and not intended to limit the scope of the appended claims. Generally according to the invention an abutment base in the form of a short tubular body has a transverse wall at a first end of the body shaped to mate with the gingival aspect of the transverse surface of the patient's implant fixture, and a through-bore from one to the other, opening through the transverse wall. This tubular body is rigid. A shoulder is provided within the body, in the through-bore, for cooperating with a bolt to fasten the tubular body to the implant fixture. On its exterior wall the abutment base has two grooves; one nearer to the transverse wall is preferably wider and shallower than the other, which is farther away from the transverse wall, and so is displaced in a supragingival direction with relation to the transverse wall. The present invention also provides a dental restoration adapted to be affixed to the abutment base, which includes a supragingivally extending rigid substructure having at its gingival end peripheral means for mating with the abutment base via the deeper and narrower groove, and an anatomical overlay covering the substructure which envelops the abutment base at its gingival end and peripherally engages in the wider and shallower groove that is nearer to the transverse wall of the abutment base. The assembled dental restoration, with the abutment base fixed in the gingival end of the substructure and its overlay, can be fastened to the implant fixture with a screw bolt engaged in the through-bore. Access to the through-bore is via a hole in the rigid substructure.

The invention generally provides a precision-machined abutment base which can be precision-fitted to the coronal aspect of a dental implant feature, and which allows a metal substructure to be cast to it, on which an anatomical overlay can be formed, e.g.: baked.

Abutment bases according to the invention may be made of a variety of rigid dental materials, preferably metals such as dental gold, as can the substructure of the restoration. The latter can be cast to the abutment base, using known dental proccesses, for example the lost wax process. The access hole in the substructure can be provided with a waxing post. In use, a restoration is fashioned around the abutment base, and a bolt is used to fasten the restoration to the implant fixture, the bolt being mainipulated through the access hole in the substructure. The access hole may then be filled with a suitable plug that is able to be drilled out later if and when access to the bolt should be required to remove the restoration from the implant fixture.

the abutment base is preferably precision machined to present a transverse wall that fits as near as possible precisely to the gingival aspect transverse surface of the patient's implant fixture. Success in this respect will prevent, hopefully eliminate, the danger of bending or breaking the bolt used to fasten the restoration to the implant fixture, a common cause of failure of single-tooth dental restorations that are mounted on dental implant fixtures in the present state of the dental art.

Other advantages and features of the invention will be apparent from the description of an exemplary embodiment of it which follows, with reference to the accompanying drawings, in which.

Figure 2:
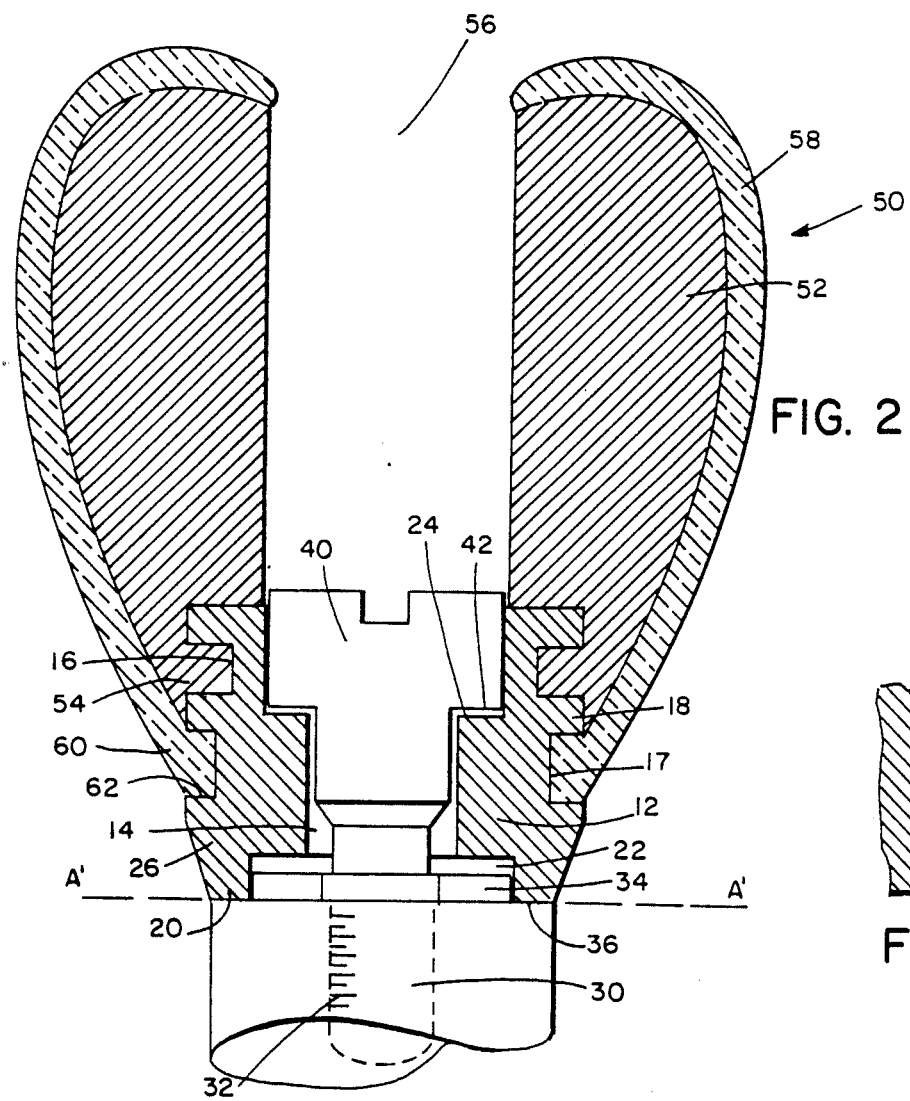
FIG. 2 illustrates the abutment base of FIG. 1 united with a dental restoration fixed to an implant fixture.

In the drawings, an abutment base 10, generally tubular in shape, has a body portion 12 with a through-bore 14. A first annular groove 16 and a second annular groove 17 in the side wall 18 are axially spaced apart. The first groove is axially narrower and radially deeper than the second groove 17. A transverse wall 20 has a non-circular; e.g: hexagonal, recess 22 in it. The second groove 17 is nearer to the transverse wall 20 than the first groove 16. A transverse shoulder 24 is provided in the through-bore 14, for cooperation with screw means (e.g.: bolt 40 in FIG. 2) to fasten the body portion 12 to an implant fixture, to be described with reference to FIG. 2.

The abutment base 10 is intended for use with a dental implant fixture of known design, exemplified by the fixture 30 shown in FIG. 2. In use, such a fixture is surgically implanted in a patient's jawbone (not shown) the gingival surface of which is indicated by a dashed line A'—A' in FIG. 2. The fixture has a non-circular (e.g: hexagonal) projection 34 on its gingival surface 36 which is normally flush or nearly flush with the gingival surface A'—A' of the patient's jawbone when the fixture is implanted in it. An internally-threaded socket 32, opening centrally through the projection 34, extends axially into the fixture 30. The recess 22 and the projection 34 have matching cross-sectional shapes and dimensions, so that when the abutment base 10 is fitted to the implant fixture 30, relative rotation between them around the axis of the socket 32 will be prevented. In use the abutment base 10 is fixed to the implant fixture 30 with the screw bolt 40, which screws into the socket 32. The head 42 of the bolt comes to rest on the shoulder 24, bringing the transverse wall 20 of the abutment base into firm contact with the gingival surface 36 of the implant fixture. The abutment base is preferably machined, out of a dental gold alloy for example, or other suitable dental metal, to assure that the meeting surface 20 and 36 are maintained in precise firm contact with each other.

To assure firm contacts, and a rigid connection between the abutment base and the implant fixture, the male projection 34 is axially shorter than the female recess 22, as is apparent in FIG. 2.

The abutment base 10 is intended for use in accurately fixing a permanent dental restoration on the dental implant fixture 30. The dental restoration shown in FIG. 2 comprises a coronal part 50 which is fixed at its gingival end to the abutment base around its side walls 18. A rigid substructure 52 of the restoration is formed in place (e.g: cast) around the body 12 of the abutment base. At its gingival end 54 the substructure engages at its periphery in the deeper first groove 16, leaving the second groove 17 exposed. A bore 56 in the substructure is coaxial with the through-bore 14 of the abutment base. The substructure may be cast of a dental gold alloy to form a unit with the abutment base. An anatomical overlay 58, made for example of dental ceramic or porcelain, covers the substructure and at its gingival end 60 and peripherally engages in the shallower but wider second groove 17. The marginal portion 26 of the body 12 between the second groove 17 and the transverse wall 20 is left exposed. The shape of the gingival end 60 of the overlay 58, where it enters the second groove 17, places a thick portion of overlay material bounding the exposed surface of the marginal portion 26 of the body 12, so that no sharp or thin marginal portion of overlay material is left at the gingival end 60, thereby removing a possible source of marginal chipping of the overlay. The boundary between the overlay 58 and the marginal portion 26 of the body 12 extends into the body 12 along a wall 62 of the second groove 17, generally transversely to the tubular axis of the abutment base 10. This provides an extended marginal contact between the overlay and the base which can be tightly sealed against failure in use.

Figure 3:
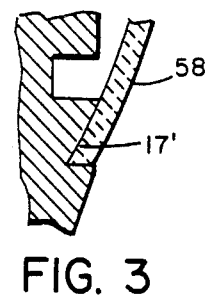
FIG. 3 shows a modification of the invention.
Figure 1A:
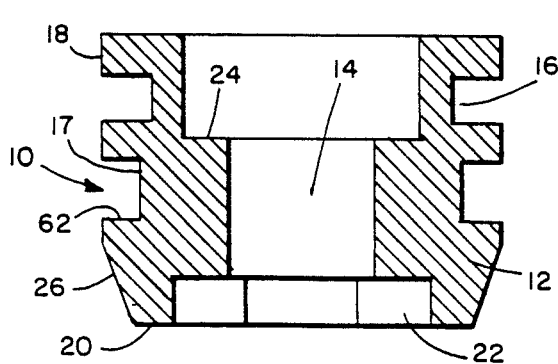
FIG. 1 shows in longitudinal and transverse sections A and B an abutment base according to the invention.
Figure 1B:
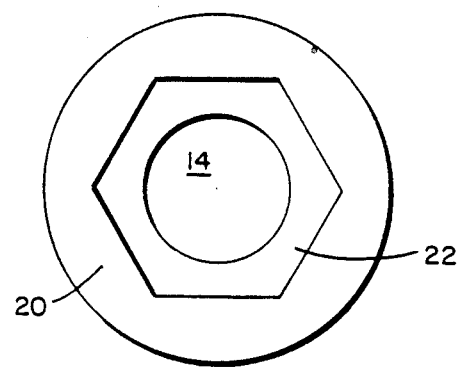

As shown in FIG. 3, the second groove 17 can be made triangular in cross section 17'.

what is claim is

1. An artifical tooth adapted for attachment to a dental implant fixture having a gingival surface through which a threaded bore opens into said fixture, said tooth including a coronal part and an abutment base engaged in a gingival portion of said coronal part, said base comprising a generally tubular rigid body having at one end a transverse wall precision-formed to mate with said gingival surface and a through-bore opening at a first end to said transverse wall, means within said through-bore providing an annular retainer for cooperating with screw means to fasten said body to said fixture via said threaded bore when said body is adjacent said fixture with said transverse wall confronting said gingival surface and said through-bore aligned with said threaded bore, first and second groove means around the sidewall of said body, the second groove means being nearer to said transverse wall than the first groove means, the gingival end of said coronal part surrounding and being affixed to said sidewall via said first and second groove means, a bore in said coronal part aligned with and giving access to said through-bore, said coronal part including a metallic substructure the gingival portion of which is engaged in said first groove means, and covering said substructure an anatomical overlay which envelopes said abutment base around its sidewall nearer to said transverse wall than said substructure, the gingival portion of said overlay being engaged in said second groove means.

2. An artificial tooth according to claim 1 in which said substructure is cast to said body, said bore in said coronal part being formed in said substructure.

3. An artificial tooth according to claim 2 in which a marginal portion of said abutment base between said second groove means and said transverse wall is not covered by any portion of said coronal part.

4. An artifical tooth according to claim 3 in which said gingival portion of said overlay has a margin with said marginal portion of said abutment base which extends substantially transversely into said second groove means so as to form an extended marginal contact along a wall of said second groove means that is substantially devoid of thin or sharp sections of overlay material, thereby forming an extended marginal seal of said overlay to said abutment base.

5. An artificial tooth according to claim 1 including interlocking means in said gingival surface and said transverse wall to prevent relative rotation between said body and said fixture around the axis of said threaded bore.

* * * * *